(12) United States Patent
Landau et al.

(10) Patent No.: US 9,796,100 B2
(45) Date of Patent: Oct. 24, 2017

(54) APPARATUS FOR CUTTING ELECTRONIC MONITORING BRACELET STRAPS

(71) Applicant: 3M INNOVATIVE PROPERTIES COMPANY, St. Paul, MN (US)

(72) Inventors: Eitan Landau, Netanya (IL); Sagiv Zeltser, Netanya (IL); Ilan Burlo, Ramat Gan (IL); Benny Sakat, Raanana (IL)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 15/432,423

(22) Filed: Feb. 14, 2017

(65) Prior Publication Data
US 2017/0157785 A1 Jun. 8, 2017

Related U.S. Application Data

(62) Division of application No. 13/746,416, filed on Jan. 22, 2013, now Pat. No. 9,566,717.

(51) Int. Cl.
  *B26B 17/00* (2006.01)
  *B26B 29/04* (2006.01)

(52) U.S. Cl.
  CPC ............ *B26B 17/006* (2013.01); *B26B 29/04* (2013.01)

(58) Field of Classification Search
  CPC .............................. B26B 17/006; B26B 29/04
  USPC ............................................................. 83/13
  See application file for complete search history.

(56) References Cited

U.S. PATENT DOCUMENTS

| | | | | |
|---|---|---|---|---|
| 1,082,385 A | * | 12/1913 | Zimmerman | ........... B26B 29/04 144/146 |
| 1,750,929 A | * | 3/1930 | Griswold | ............. A43D 100/02 30/363 |
| 2,223,164 A | | 11/1940 | Childress | |
| 2,340,937 A | * | 2/1944 | Curtis | ..................... B26B 5/008 30/131 |

(Continued)

FOREIGN PATENT DOCUMENTS

| | | |
|---|---|---|
| CH | 252 623 | 1/1948 |
| DE | 25 36 109 | 2/1977 |

(Continued)

OTHER PUBLICATIONS http://www.eay.com/itm/WONDER-BUNDLER-BUNDLING-STRAP-DISPENSER-NIB-/350276895778, © 1995-013 eBay Inc.

(Continued)

*Primary Examiner* — Sean Michalski

(57) ABSTRACT

The present disclosure includes a cutting apparatus for cutting a strap to a desired length. The cutting apparatus includes a handle body with first and second handles and a head affixed to the handle body. The head includes an attachment mechanism to allow a strap to be cut to be releasably secured to a first end the head. The cutting apparatus further includes a blade disposed proximate to a second end of the head. The length of the head or the distance between the first end of the head and the blade approximates a device body length. The present disclosure further includes a method of using a handheld cutting apparatus for cutting a strap to a desired length, such that the combined length of the strap and a device to be attached to an object, approximates the circumference of the object.

6 Claims, 3 Drawing Sheets

(56) References Cited

U.S. PATENT DOCUMENTS

| | | | | |
|---|---|---|---|---|
| 2,734,569 A * | 2/1956 | Neudauer | ............... | B41B 11/00 33/666 |
| 3,261,096 A * | 7/1966 | Klenk | ................... | B23D 29/02 30/242 |
| 4,227,305 A * | 10/1980 | Newman | ................. | B26B 13/10 30/229 |
| 4,459,717 A * | 7/1984 | Halstead | ................ | B25B 25/00 30/250 |
| 4,488,358 A * | 12/1984 | Leggett, Jr. | ............ | B26D 7/015 30/233 |
| RE32,460 E * | 7/1987 | Leggett, Jr. | ............ | B26D 7/015 30/233 |
| 4,776,096 A * | 10/1988 | Chang | ..................... | B26B 29/04 30/229 |
| 4,876,795 A * | 10/1989 | Chun-cheng | ........... | B26B 13/06 30/229 |
| 4,899,134 A * | 2/1990 | Wheeless, Jr. | ......... | A61B 17/12 340/539.1 |
| 5,006,830 A * | 4/1991 | Merritt | ................... | A61B 17/12 283/75 |
| 5,226,236 A * | 7/1993 | Harrington, III | ........ | A01G 3/02 30/131 |
| 5,309,802 A * | 5/1994 | Mammosser | ........... | B26B 27/00 30/278 |
| D356,516 S * | 3/1995 | Price | ....................... | B26B 27/00 D10/104.1 |
| 5,504,474 A | 4/1996 | Libman | | |
| 5,535,932 A * | 7/1996 | Ruczienski | ............. | B26B 27/00 225/1 |
| 5,542,182 A * | 8/1996 | Martinez | ................. | B26B 17/00 30/178 |
| 5,609,716 A | 3/1997 | Mosher, Jr. | | |
| 5,731,757 A | 3/1998 | Layson, Jr. | | |
| 5,740,612 A * | 4/1998 | Takeshita | ................ | B26B 27/00 30/1.5 |
| 5,831,535 A | 11/1998 | Reisman | | |
| 5,832,612 A * | 11/1998 | Cornell | ................... | B26B 13/10 30/229 |
| 5,936,529 A | 8/1999 | Reisman | | |
| 6,145,203 A * | 11/2000 | Appleman | ........... | B23D 29/026 30/131 |
| 6,388,612 B1 * | 5/2002 | Neher | ................... | G01S 5/0018 224/164 |
| 6,684,761 B2 | 2/2004 | Yu Chen | | |
| 6,840,078 B1 * | 1/2005 | Clover | ................. | B21D 28/243 30/134 |
| 6,847,295 B1 * | 1/2005 | Taliaferro | .......... | G08B 21/0211 340/539.1 |
| 6,973,725 B2 * | 12/2005 | Lai | .......................... | B26B 13/22 30/179 |
| 7,194,937 B1 | 3/2007 | Melkowits | | |
| 7,421,788 B2 * | 9/2008 | Gardner | ................... | B25G 3/38 30/131 |
| 7,474,592 B2 | 1/2009 | Lyon | | |
| 7,581,320 B2 * | 9/2009 | Achiwa | .................. | B26B 13/22 156/304.1 |
| 7,636,047 B1 * | 12/2009 | Sempek | ................. | G08B 21/22 340/572.1 |
| D625,978 S * | 10/2010 | Zeng | ....................... | B26B 27/00 D7/693 |
| 8,424,716 B2 | 4/2013 | Hegan | | |
| 9,572,579 B2 * | 2/2017 | Weisshaupt | ........ | A61B 17/1227 |
| 2002/0020067 A1 * | 2/2002 | Silver | ..................... | B26B 13/00 30/226 |
| 2002/0035786 A1 * | 3/2002 | Gilder | ................. | B26B 21/4018 30/50 |
| 2005/0097758 A1 * | 5/2005 | Elkins | .................... | B26B 17/00 30/233 |
| 2006/0075642 A1 * | 4/2006 | Elkins | .................... | B26B 17/00 30/233 |
| 2007/0204470 A1 * | 9/2007 | Lai | .......................... | B26B 17/00 30/244 |
| 2008/0266118 A1 * | 10/2008 | Pierson | ................ | A61B 5/0205 340/573.6 |
| 2009/0182216 A1 * | 7/2009 | Roushey, III | ...... | A61B 5/14546 600/364 |
| 2009/0183372 A1 * | 7/2009 | Oriet | ...................... | B26D 3/169 30/92 |
| 2010/0152564 A1 * | 6/2010 | Nguyen | ............... | A61B 5/0444 600/390 |
| 2010/0162572 A1 * | 7/2010 | Kelly | ..................... | B26B 13/08 30/124 |
| 2010/0206148 A1 * | 8/2010 | Reyes | ..................... | B26B 27/00 83/53 |
| 2010/0217096 A1 * | 8/2010 | Nanikashvili | ...... | A61B 5/02438 600/301 |
| 2010/0240967 A1 * | 9/2010 | Kim | ..................... | A61B 5/02055 600/301 |
| 2010/0258606 A1 * | 10/2010 | Wu | ......................... | B26B 27/00 225/58 |
| 2010/0293720 A1 * | 11/2010 | Zhang | .................. | B25B 27/10 7/125 |
| 2010/0327002 A1 * | 12/2010 | Hegan | .................... | G09F 3/005 221/30 |
| 2011/0174235 A1 * | 7/2011 | Vinano | .................. | A01K 79/02 119/712 |
| 2011/0260870 A1 * | 10/2011 | Bailey | ................. | A61B 5/0002 340/573.1 |
| 2012/0179067 A1 * | 7/2012 | Wekell | ................ | A61B 5/4848 600/587 |
| 2013/0139392 A1 * | 6/2013 | Wright | ................. | B26B 25/005 30/278 |
| 2013/0139661 A1 * | 6/2013 | Wright | ................. | B26B 25/005 83/13 |
| 2014/0041195 A1 * | 2/2014 | Hoang | ..................... | B25B 7/12 29/434 |
| 2015/0238235 A1 * | 8/2015 | Tuten | .................. | A61B 17/7077 606/279 |
| 2015/0258302 A1 * | 9/2015 | Chandra | ............... | A61M 21/02 600/27 |

FOREIGN PATENT DOCUMENTS

| | | |
|---|---|---|
| DE | 29 706 615 | 7/1997 |
| FR | 2 843 904 | 8/2002 |
| WO | WO 03/054814 | 7/2003 |

OTHER PUBLICATIONS

International Search Report for International Application No. PCT/US2014/012520 dated Jun. 24, 2014.

* cited by examiner

APPARATUS FOR CUTTING ELECTRONIC MONITORING BRACELET STRAPS

CROSS REFERENCE TO RELATED APPLICATION

This application is a divisional of U.S. application Ser. No. 13/746,416, filed Jan. 22, 2013, the disclosure of which is incorporated by reference in its entirety herein.

TECHNICAL FIELD

A cutting apparatus for cutting a strap to a desired length. More specifically, a handheld cutting apparatus for cutting a strap used to secure an electronic monitoring device to a monitored individual.

BACKGROUND

Electronic monitoring devices are used by many government and private entities to detect and monitor the location of individuals wearing or associated with an electronic monitoring device. Electronic monitoring devices provide a cost effective solution to overcrowding of jails or prisons, and are often used to allow non-violent offenders to transition to society during a parole period, after being incarcerated for a period of time. Such devices can ensure confinement of the offender or monitored person to a particular location, such as at the offender's place of residence or at a rehabilitating institution, and may also determine whether the individual enters any place they are not allowed, also referred to as exclusion zones.

Electronic monitoring devices typically use either radio frequency (RF) communication with a second device, or Global Positioning System (GPS) technology to confirm the location of a monitored person, either in an absolute sense as with GPS, or relative to the second device with which the electronic monitoring device is in RF communication.

Electronic monitoring devices or systems typically include at least one component that is attached to the individual being monitored. The most traditional method of attachment is to secure the device around one of the individual's limbs, such as the ankle, with a strap. It is important that the strap and monitoring device fit securely about the limb so the device cannot be easily removed by the monitored individual. At the same time, it is important that the device is not too tight so that it is uncomfortable or causes skin irritation. Improvements in ensuring appropriate fit of monitoring devices secured to individuals would be welcomed.

SUMMARY

The current invention provides a handheld cutting apparatus that allows a strap to be cut to desired length. In particular, the cutting apparatus of the present disclosure is configured to cut a strap to secure an electronic monitoring device to an individual with a secure fit. In many instances it can be difficult to cut a strap to secure a monitoring device to a monitored individual to an appropriate length due to variation in the circumference of the limb to which the device is to be installed along with the length of the monitoring device to be attached to the strap. In other words, because the monitoring device will extend along a portion of the circumference of the limb, the individual cutting the strap cannot simply wrap the strap about the circumference of the object or limb, and cut it to that length. They must also estimate the length of the monitoring device, and adjust the length of the strap accordingly.

The apparatus of the present invention provides significant advantages to address these difficulties. The cutting apparatus allows a parole officer or other individual attaching the monitoring device to the offender to cut the strap to the appropriate length without prior measurement. Additionally, use of the present invention reduces waste by allowing the strap to be cut to the appropriate length, not to be too long, using excess material, or too short, requiring a newly cut strap. Further, when officers or individuals are attaching such a monitoring device to a released offender, in current attachment processes, officers are reticent to cut the strap to the appropriate length in the presence of the offender due to concern about the danger of using scissors or another cutting tool with an exposed blade being turned into a weapon. The present invention provides a safe efficient cutting mechanism, reducing waste and increasing safety.

In one aspect, the present invention includes a handheld cutting apparatus for cutting a strap to a desired length. The cutting apparatus includes a handle body including a first handle and a second handle and a head affixed to the handle body. The apparatus further includes an attachment mechanism on a first end of the head to secure the strap to the head and a blade disposed proximate to a second end of the head, the blade being configured to cut the strap, wherein the distance along the head between the first end of the head and the blade approximates a device body length.

In another aspect, the present invention includes a handheld cutting apparatus for cutting a strap to a desired length. The apparatus includes a handle body including a first handle and a second handle and a head affixed to the handle body, wherein the head has a length that approximates a device body length. The apparatus further includes a blade disposed proximate to an end of the head, the blade being configured to cut the strap and a clamp disposed between the handles.

In another aspect, the present invention includes a method of using a handheld cutting apparatus for cutting a strap to a desired length, such that the combined length of the strap and a device to be attached to an object, approximates the circumference of the object. The method includes securing a first end of the strap to a first end of a head, the head having a length approximating the length of the device to be attached to the strap, the head being attached to a handle body. Further, the method includes wrapping the strap around the circumference of the object and inserting a second end of the strap into a cutting slot in the handle body proximate to a second end of the head. The method additionally includes cutting the strap by squeezing the first handle and the second handle toward each other.

In another aspect, the present invention includes a handheld cutting apparatus for cutting a strap to a desired length, including a handle body including a first handle and a second handle, wherein the first handle is connected to a cutting blade and the second handle is connected to a cutting surface; wherein the first and second handles are affixed to one another by a pivot member that allows the cutting blade and the cutting surface to come into contact with one another. The apparatus also includes a head attached to the handle body, the head including an opening sized to accept and hold a clip attached to a first end of the strap. The head has a length that approximates a device body length.

BRIEF DESCRIPTION OF DRAWINGS

The invention may be more completely understood in consideration of the following detailed description of various embodiments of the invention in connection with the accompanying drawings, in which.

In the following description of the illustrated embodiments, reference is made to the accompanying drawings, in which is shown by way of illustration, various embodiments in which the invention may be practiced. It is to be understood that the embodiments may be utilized and structural changes may be made without departing from the scope of the present invention. The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
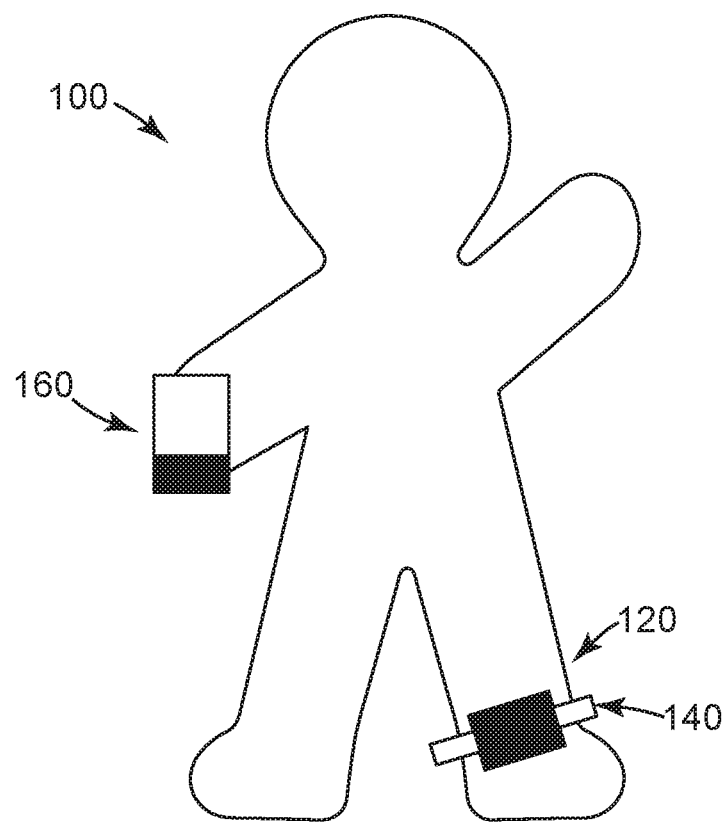
FIG. 1 is an example of a monitoring device secured to an individual with a strap.

FIG. 1 is an example of a monitoring device 120 secured to an individual 100 with a strap 140. The individual 100 may be a released offender or other person requiring surveillance or monitoring such as a juvenile or child. While the electronic monitoring device 120 is illustrated as being attached to an ankle of individual 100, the electronic monitoring device 120 and strap 140 may be attached to the wrist, arm, or connected to a belt of an individual 100. Various attachment mechanisms, other than strap 140, and placement of the electronic monitoring device 120 on the body will be apparent to one of skill in the art. Tamper detection mechanisms may be designed in the strap 140 and electronic monitoring device 120 as further illustrated in FIG. 2. U.S. Pat. Nos. 5,504,474; 5,731,757; 5,831,535; and 5,936,529 disclose tamper mechanisms for use with the electronic monitoring device 120 and strap 140 and are incorporated herein by reference. Monitoring device 140 may have a variety of capabilities and components. In a first configuration, monitoring device 140 may have radio frequency (RF) communication capabilities, and may be designed to communicate with a stationary unit, such as a home monitoring unit. In this configuration, the home monitoring unit is able to confirm the presence of the monitored individual 100 when the monitoring device 140 is within communication range of the home monitoring unit. This configuration may be used in curfew monitoring or other similar situations. In a second configuration, the monitoring device 140 may have GPS or other location capabilities in addition to the RF capabilities described above. This allows the monitoring device 120 to determine its location when it is outside of a communication range of a home monitoring unit. Monitoring device 120 may use other location technologies, such as WIFI, zigbee or other technologies that will be apparent to one of skill in the art. Monitoring device 120 may also transmit its location to a central monitoring center via some form of wireless communication. In a third configuration, monitoring device includes only RF (or some equivalent) communication capabilities, and communicates with handheld device 160 to confirm that the two devices are within the appropriate range of each other. Handheld device 160 may then include other location capabilities, such as GPS functionality. While these are three common configurations for the monitoring devices shown in FIG. 1, other configurations and communication with a variety of other devices are also possible and apparent. Communication may occur between handheld device 160, monitoring device 120 and other devices such as a computer, PDA, home base unit, central monitoring system, or other processing machine. It will be easily appreciated by persons skilled in the art that other types of wireless communication techniques, such as infrared, may be used as well.

Figure 2:
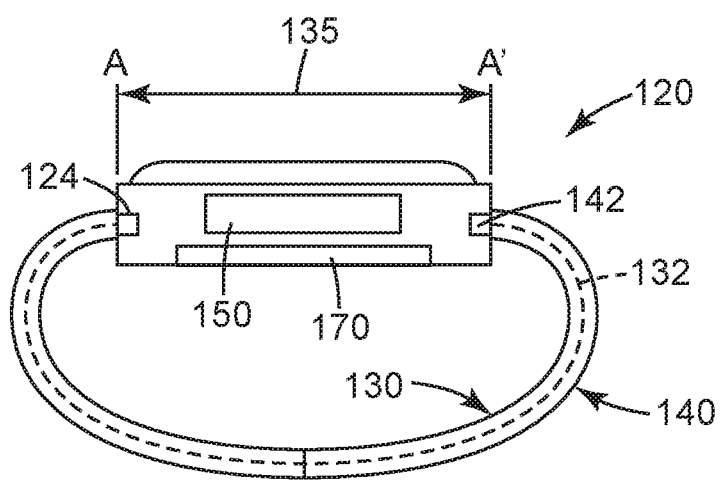
FIG. 2 is a cross section of an exemplary monitoring device and strap.

FIG. 2 is a cross section of an exemplary monitoring device 120 and strap 140. As described, monitoring device 120 may include a variety of electronic components and capabilities. One such component is tamper mechanism 132 in strap 140. Tamper mechanism 132 may be, for example, a fiber optic cable to allow transmission of an electronic signal in a circuit formed through monitoring device 120 and the circumference of the monitoring device 140. As shown, strap 140 is attached to the monitoring device at receive opening 124. There are a variety of configurations that allow such attachment. In one embodiment, strap 140 has a clip 142 attached to each end of strap 140. The clips 142 are configured to be inserted into receive openings 124 on each side or end of monitoring device 120. Receive openings 124 may include locking mechanisms such that, once attached to monitoring device 120, strap 140 cannot be detached from monitoring device 120 without breaking at least one of clips 142 or strap 140. Clips 142 can be designed to facilitate electrical contact between a tamper mechanism 132 such as a fiber optic cable in strap 140 and an electrical interface in monitoring device 120. These electrical connections can create a complete circuit that, when broken or disconnected, can be indicative of tamper with monitoring device 120. Clips 142 may be designed to align strap 140 with receive opening 124 to allow direct electrical connection between a tamper mechanism 132 in strap 140 and receive opening 124, or they may include metal or electrically conductive features or components to complete such electrical connection. While this is one way in which strap 140 may be connected to monitoring device 120, a variety of configurations may be used. For example, receive opening 124 may hold strap 140 in place by use of pressure, pins included in receive opening 124, welding, or other methods as will be apparent to one of skill in the art upon reading the present disclosure. In another configuration, strap 140 may be connected to monitoring device 120 without the use of receive opening 124, but instead by other fixtures or features that secure the two components together.

Monitoring device 120 may also include bio sensor 170 that detects skin in proximity to bio sensor 170 by detecting reflected light off of the skin. Electronics module 150 can house various electronics and communication components required to facilitate monitoring and other features as discussed in the present disclosure.

As discussed, one important feature of effective monitoring of an individual is ensuring a good fit of monitoring device 120 with strap 140 to the limb of the individual. As discussed throughout this application, the combined length of monitoring device 120 and strap 140 is not considered to be an end-to-end measurement, but instead, the inner circumference 130 of the two components when attached to each other. There may be overlap between an end of strap 140 and an end of device 120 to allow strap 140 to be attached to device 120. Such overlap may range based on the device, but may be less than 5 mm, 10, mm, 15 mm or 20 mm. Further, the body length of monitoring device 120 is approximately the distance 135 between the two ends A and A' of monitoring device 120 attached to the two ends of strap 140.

Figure 3:
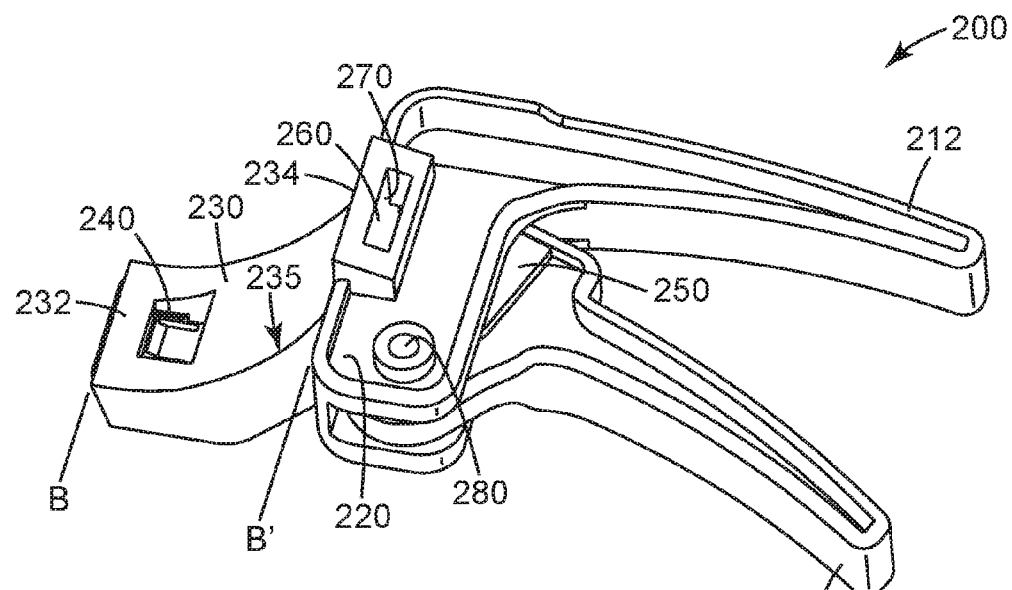
FIG. 3 is an exemplary handheld cutting apparatus.

FIG. 3 is an exemplary handheld cutting apparatus 200. Cutting apparatus 200 includes handle body 210, including first handle 211 and second handle 212. Head 230 is affixed to handle body 210, and in some embodiments, may be manufactured as a single piece with handle body 210. In some configurations, head 230 may be removably attached to handle body 210 such that different heads can be interchangeably attached to handle body 210. Different heads could be used based on different devices and different device sizes. Head 230 includes first end 232 and second end 234. First end 232 includes an attachment mechanism 240 used to secure a strap to head 230. Attachment mechanism 240 may be an opening sized to accept and hold a clip attached to a first end of the strap, or may be any other component as will be apparent to one of skill in the art used to releasably secure the strap to the head 230.

A strap may be a strap used in conjunction with an electronic monitoring device as illustrated in FIG. 2, or it may be a strap used for any other sort of device to be attached with a close fit to an object. For example, such an item may include an identification device, an access tag, or any other sort of device to be secured to an object.

Cutting apparatus 200 further includes a blade 250 disposed near second end 234 of head 230. In some configurations, blade 250 may protrude from a surface of first handle 211. In one configuration, the distance 235 along head 230 between the first end 232 of head 230 and blade 250, represented as the distance between B and B', approximates a device body length, such as a monitoring device or other device to be secured to an object. In other configurations, head 230 has a length that approximates a device body length.

Handle body 210 can include a first handle 211 and second handle 212. In some configurations, first handle 211 is connecting to a cutting blade 250, and the second handle 212 is connected to a cutting pad 270. In one configuration, the first handle 211 and second handle 212 are affixed to one another by a pivot member 280 that allows the cutting blade 250 and the cutting pad 270 to come into contact with one another.

Handle body 210 includes a protective wall 220 extending parallel to blade 250. Protective wall 220 may include a slot 260 to allow a strap to pass through the slot into an area between blade 250 and cutting pad 270, such that when a user squeezes the first handle 211 and second handle 212 toward each other, the blade 250 cuts the strap.

Figure 4:
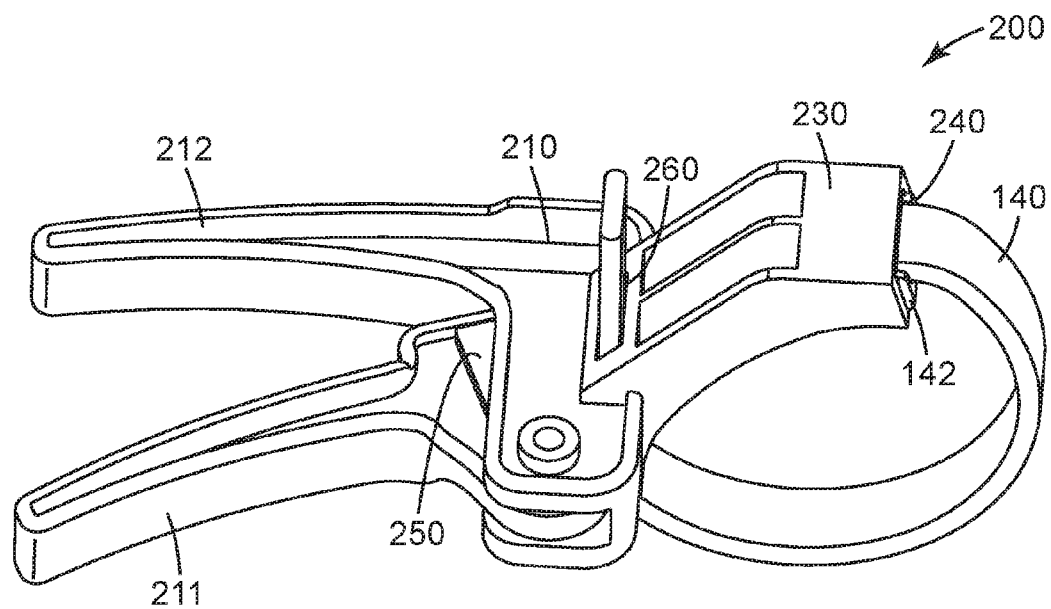
FIG. 4 is an exemplary handheld cutting apparatus shown cutting a strap.

FIG. 4 is an exemplary handheld cutting apparatus 200 shown cutting a strap 140. As described elsewhere, cutting apparatus 200 includes handle body 210, cutting blade 250, head 230, attachment mechanism 240 and slot 260 through protective wall 220. In FIG. 4, clip 142 attached to a first end of strap 140 is inserted into attachment mechanism 240 to secure the strap to a first end of head 230. The second or opposite end of strap 140 extends from head 230 and inserted past blade 250 and through slot 260 in protective wall 220. The combination of head 230 and strap 140 collectively form a circumference that approximates a circumference of an object to which a device is to be attached, using strap 140. Strap 140 is positioned such that blade 250 will cut strap 140 to a desired length by squeezing the first handle 211 and the second handle 212 toward each other.

Figure 5:
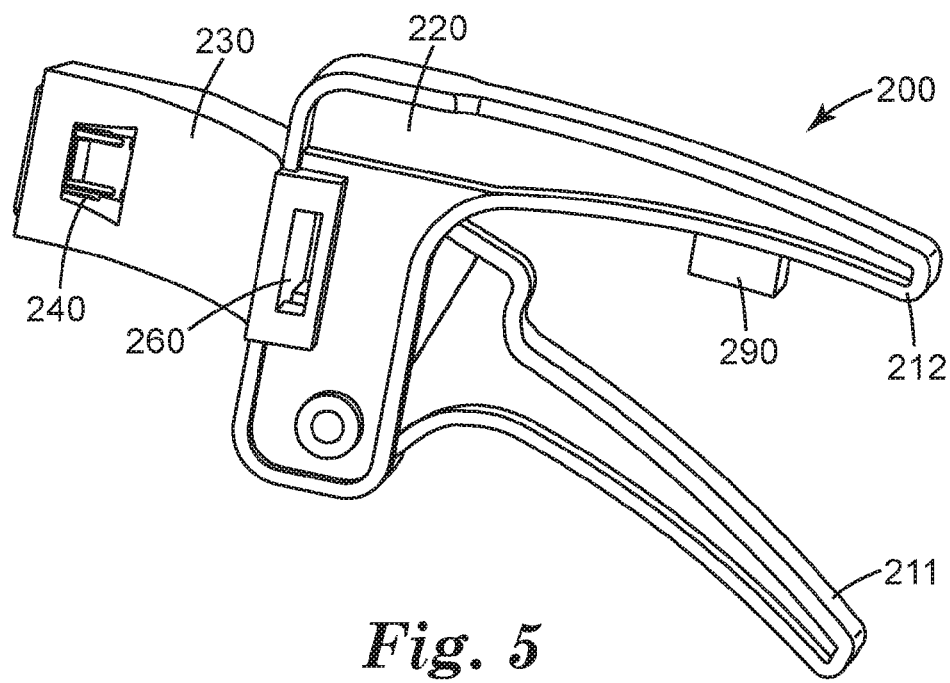
FIG. 5 is an exemplary handheld cutting apparatus including a clamp.

FIG. 5 is an exemplary handheld cutting apparatus 200 including a clamp 290. In some embodiments where a clip is attached to the end of a strap, it can be difficult to attach the clip to the strap manually without the use of tools given the density (thickness and rigid construction) of a strap. To enable a user of the present cutting apparatus 200 to attach a clip to an end of a strap with greater ease, some embodiments of cutting apparatus 200 include clamp 290 disposed between first handle 211 and second handle 212. To use clamp 290, a clip and an end of a strap can be positioned in the appropriate location relative to each other. The clip may include pins that penetrate the strap. The clip and strap can then be placed between first handle 211 and second handle 212 in the area of clamp 290. When a user squeezes first handle 211 and second handle 212 together, clamp 290 can be used to force pins in a clip through the material of a strap, or to otherwise attach a clip to a strap where such attachment process requires clamping pressure. Clip may also be attached to strap 140 by other methods, such as using a hard glue or other attachment means.

Figure 6:
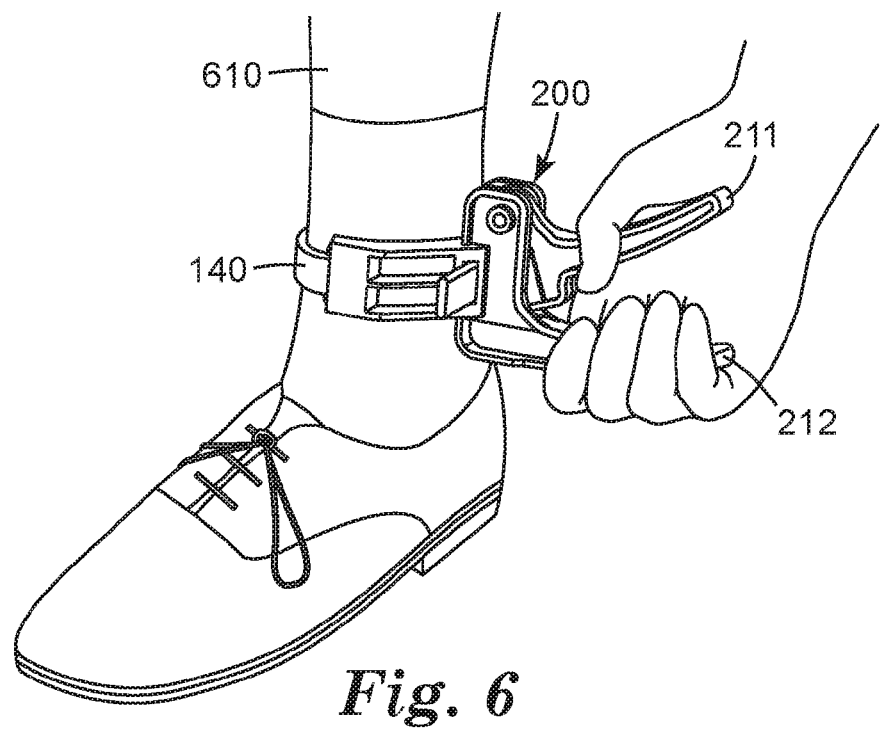
FIG. 6 is an example of a handheld cutting apparatus cutting a strap to a desired length.

FIG. 6 is an example of a handheld cutting apparatus 200 cutting a strap 140 to a desired length. Handheld cutting apparatus 200 may generally be used to cut a strap 140 to a desired length, such that the combined length of the strap 140 and a device to be attached to an object (such as leg 610) approximates the circumference of the object.

Such a method of use generally comprises securing a first end of the strap 140 to a first end of head 230. The head 230 generally approximates the length of a device to be secured to an object by attaching the device to strap 140. The head 230 is generally attached to handle body 210.

After the strap 140 is secured to head 230, the strap is wrapped around the circumference of the object to which the device is to be attached, such as leg 610 as illustrated. The strap is intended to be wrapped securely about the object or leg 610 to prevent a monitored individual from being able to slide the device off without disconnecting strap 140 from the device. In some embodiments, the combined length of the strap 140 and monitoring device, which is approximately equivalent to the combined length of the head 230 and strap as measured by the inner circumference is no more than five percent greater than the circumference of the object to which the monitoring device is attached. In other embodiments, the combined inner circumference of the strap and device body may be slightly greater to accommodate, for example, wearing a sock or other article of clothing underneath the monitoring device. For example, the combined inner circumference may be about ten percent or fifteen percent greater than the circumference of the object to which the monitoring device is to be attached.

After the strap 140 is wrapped about the circumference of the object, the strap can be cut to the appropriate length by inserting a second end of strap 140 through cutting slot 260. A user can then cut the strap 140 by squeezing first handle 211 and second handle 212 toward each other.

After the strap 140 is cut to the desired length, the first end of strap 140 may be removed from the attachment mechanism in head 230, which may include removing a clip from an opening in head 230. In the case where the device to be attached to the object is configured with receive openings on each end to mate with the clip attached to the strap 140, a second clip may be attached to the second end of strap 140.

Attaching the device to a limb of an individual to be monitored may include attaching the first end of the strap 140 to a first end of the device; wrapping the strap around the circumference of the object or limb, and attaching the second end of the strap 140 to a second end of the device.

In some embodiments, strap 140 may include a tamper mechanism such that if strap 140 is disconnected from the device after it has been initially attached, the device will send a communication to a central monitoring system or otherwise register, store or communicate an alarm indicative of tamper.

While the method described above indicates the process of cutting strap 140 when beginning with a finite length of strap 140, the present invention may also be used when working with a roll of strap 140 to cut strap 140 to a desired length. When working with a roll of strap 140, a user can first insert the strap 140 through cutting slot 260. A clip is then attached to strap 140, and strap 140 is wrapped about the circumference of an object or limb.

After strap 140 is wrapped about the object or limb, the strap 140 can be attached to attachment mechanism in head 230. The portion of strap extending through slot 260 can then be pulled to the appropriate tightness, and a user can cut strap 140 to the appropriate length by squeezing the handles together. The strap 140 can then be used to attach a device to a monitored individual as elsewhere described.

While the present disclosure describes a particular embodiment of the present inventions, variations on the present invention will be apparent to one of ordinary skill in the art upon reading the disclosure. For example, a handle body in a cutting apparatus may take a variety of configurations. A variety of safety mechanisms in addition to or instead of a protective wall may be used to limit potential exposure of a blade in such a handheld cutting apparatus. Other variations will be apparent, and are intended to be included within the scope of the present disclosure.

What is claimed is:

1. A method of using a handheld cutting apparatus for cutting a strap to a desired length, such that the combined length of the strap and a device to be attached to an object, approximates the circumference of the object, the method comprising:
    securing a first end of the strap to a first end of a head, the head having a length approximating the length of the device to be attached to the strap, the head being attached to a handle body;
    wrapping the strap around the circumference of the object;
    inserting a second end of the strap into a cutting slot in the handle body proximate to a second end of the head;
    cutting the strap by squeezing the first handle and the second handle toward each other.

2. The method of claim 1, further comprising attaching a clip to the first end of the strap prior to securing the first end of the strap to the first end of the head.

3. The method of claim 2, wherein the clip is configured to mate with a receive opening in the device.

4. The method of claim 1, wherein the device is an electronic monitoring device and wherein the object is a limb of an individual being monitored.

5. The method of claim 1, further comprising attaching the first end of the strap to a first end of the device; wrapping the strap around the circumference of the object, and attaching the second end of the strap to a second end of the device.

6. The method of claim 1, wherein the strap includes a tamper mechanism.

* * * * *